United States Patent [19]

Woodrow et al.

[11] 4,050,824

[45] Sept. 27, 1977

[54] METHOD AND APPARATUS FOR INSPECTING BOTTLED GOODS

[75] Inventors: Arthur F. Woodrow; Jorge E. Simmons, both of Tucson, Ariz.

[73] Assignee: TSN Company, Inc., Tucson, Ariz.

[21] Appl. No.: 700,013

[22] Filed: June 25, 1976

Related U.S. Application Data

[63] Continuation-in-part of Ser. No. 534,168, Dec. 19, 1974, abandoned.

[51] Int. Cl.² ............................................ G01N 21/24
[52] U.S. Cl. .................................... 356/197; 209/73; 209/111.5; 250/223 B; 356/240
[58] Field of Search ............................ 209/73, 111.5; 250/223 B; 356/196, 197, 240

[56] References Cited

U.S. PATENT DOCUMENTS

| | | | |
|---|---|---|---|
| 2,331,277 | 10/1943 | Stout | 356/197 |
| 2,531,529 | 11/1950 | Price | 356/197 |
| 3,356,853 | 12/1967 | Rottmann | 250/223 B |
| 3,627,423 | 12/1971 | Knapp | 356/197 |
| 3,830,969 | 8/1974 | Hofstein | 356/197 |

*Primary Examiner*—John K. Corbin
*Attorney, Agent, or Firm*—Cahill, Sutton & Thomas

[57] ABSTRACT

A method and apparatus are disclosed for automatically inspecting bottled goods for foreign matter as the bottles pass through bottling machinery. The inspection procedure ignores false indications of foreign matter by comparing results of a plurality of coincidentally performed inspections.

13 Claims, 4 Drawing Figures

METHOD AND APPARATUS FOR INSPECTING BOTTLED GOODS

The present application is a continuation-in-part application of a pending patent application entitled "Method and Apparatus for Inspecting Bottled Goods", filed on Dec. 19, 1974, and assigned Ser. No. 534,168, now abandoned, which describes an invention invented by the present inventors and assigned to the present assignee.

This invention relates to inspection devices for detecting foreign matter in closed containers and, in particular, to a method and apparatus for automatically detecting foreign matter in bottled beverages.

The presence of foreign matter in bottled goods is a particular problem for the bottled beverage industry. The failure to detect the presence of foreign matter in a bottled beverage not only results in a loss in customer appeal, it also may subject the bottler to substantial claims for damages by consumers. Where returnable bottles are cleaned and refilled, the problem is exacerbated since bottles are often returned with a wide variety of foreign matter disposed within them. In the past, foreign matter such as cigarettes, cigar butts, mice, paper, animal droppings, etc. have been shipped as part of the bottled beverage. In addition, the bottling process itself can introduce a variety of foreign matter into the bottled beverage. For example, the capping operation may clip the rim of the bottle, which chips fall into the liquid contained within the bottle. Even if these foreign bodies do not pose a health hazard from a bacteriological standpoint, or even pose a visual revulsion by the consumer, the presence of glass chips, or similar materials pose a definite threat of injury to the consumer.

The inspection of filled beverage bottles was for many years done visually by human operators. The filled bottles were placed over a light source and the contents visually inspected for any foreign matter. In U.S. Pat. No. 2,132,447, issued to G. T. Stout in 1938, and assigned to the Coca Cola Company, a process and apparatus for automatically inspecting bottled goods was disclosed. The disclosed process relied upon rotation of the liquid filled bottle followed by the rapid stopping of the bottle which produced a relative rotational motion of the contents of the bottle. A beam of light was then passed through the bottle and picked up by a photoelectric cell. Any interruption in the light beam was indicative of the presence of foreign matter.

To prevent any false indication of foreign matter due to defects or dirt on the exterior of the bottle, the inspecting beam and photoelectric cell were made to move at the translational speed of the bottle so that no relative movement between the bottle and the inspection apparatus took place during the inspection process. Using this process, it was necessary to move the light source at the speed of the container during the test and then return it to inspect the next container by a retrograde movement of the inspection apparatus. The inertia required to stop the inspection apparatus and return it to its original position placed a significant limitation upon the speed of the inspection process.

Alternatively, Stout disclosed keeping the inspection apparatus fixed and bringing each bottle to an abrupt stop immediately prior to the inspection process. Once again, a limitation on operating speed was introduced by this process since each bottle must be brought to a stop and then accelerated to the translational speed of the conveyor system moving the bottles through the bottling process.

A subsequent U.S. Pat. No. 2,317,559, issued to G. T. Stout, et al. in 1943 and also assigned to the Coca Cola Company, suggested that the high speed rotation of the bottle would not immediately produce a rotational speed of the liquid contents comparable to the rotational speed of the bottle. Hence, the bottle had to be rotated for a substantial period of time to overcome the inertia of the contents and permit the contents to reach the rotational speed of the container. As a result of the speed differential between the contents and the container, the method disclosed in the 1943 Stout patent differentiates between the disturbance of the inspecting light beam caused by the bottle and the distrubance caused by any foreign matter revolving with the contents.

In addition, the method disclosed in the 1943 Stout patent provides for movable inspection means so that during the inspection period, both the optics of the system and the bottle would be traveling together with no relative speed therebetween. Once again, this method requires movement of the inspection apparatus which imposes an operating speed limitation due to the built-in inertia which must be overcome to move the inspection apparatus back to its starting point. In addition, a series of frequency filters must be introduced in the light amplification system of the inspection and detection apparatus to eliminate the effects of the light passing through the bottle. This introduces additional equipment which is subject to error as well as additional expense.

In his later U.S. Pat. No. 2,646,715 issued in 1949, Mr. Stout disclosed apparatus for visually inspecting the contents of bottled goods for the presence of foreign matter. The apparatus relied upon the use of polarized light and the "Tyndall Effect". The Tyndall Effect is a complicated phenomenon, which can be illustrated by a beam of sunlight entering a darkened room and illuminating otherwise invisible particles of airborne dust. Because this inspection apparatus required a visual inspection by an operator, it can be readily appreciated that the apparatus described in Stout's 1949 patent is severly limited in operating speed.

Other U.S. Patents which disclose related systems are the following:

U.S. Pat. Nos.:

2,192,580 Sachtleben
2,253,581 Reynolds
2,331,277 Stout
2,531,529 Price
2,635,194 Kellogg et al.
2,677,304 Wallingford
3,356,853 Rottmann
3,528,544 Noguchi et al.
3,529,167 Calhoun
3,581,101 Neeff
3,590,256 Neeff
3,627,423 Knapp
3,708,680 Calhoun
3,739,184 Katsumata
3,758,215 Paruolo et al.
3,765,533 Stephens
3,777,169 Walter
3,830,969 Hofstein It is therefore an object of our invention to provide for high speed inspection of bottled goods.

It is also an object of our invention to provide for the inspection of bottled goods without the necessity of altering the translational speed of the bottled goods.

It is yet another object of our invention to provide for the inspection of bottled goods with inspection apparatus that is fixed in position.

It is a further object of our invention to provide inspection apparatus for bottled goods which employs a plurality of coincidentally performed inspections.

It is a still further object of our invention to provide inspection apparatus for bottled goods which compares the results of coincidentally performed inspections.

It is a yet further object of our invention to provide inspection apparatus for bottled goods which distinguishes between complete, partial and no blockage of coincidentally performed inspections.

Further objects and features of our invention will appear when read in conjunction with the accompanying disclosure and drawings, wherein.

Figure 1:
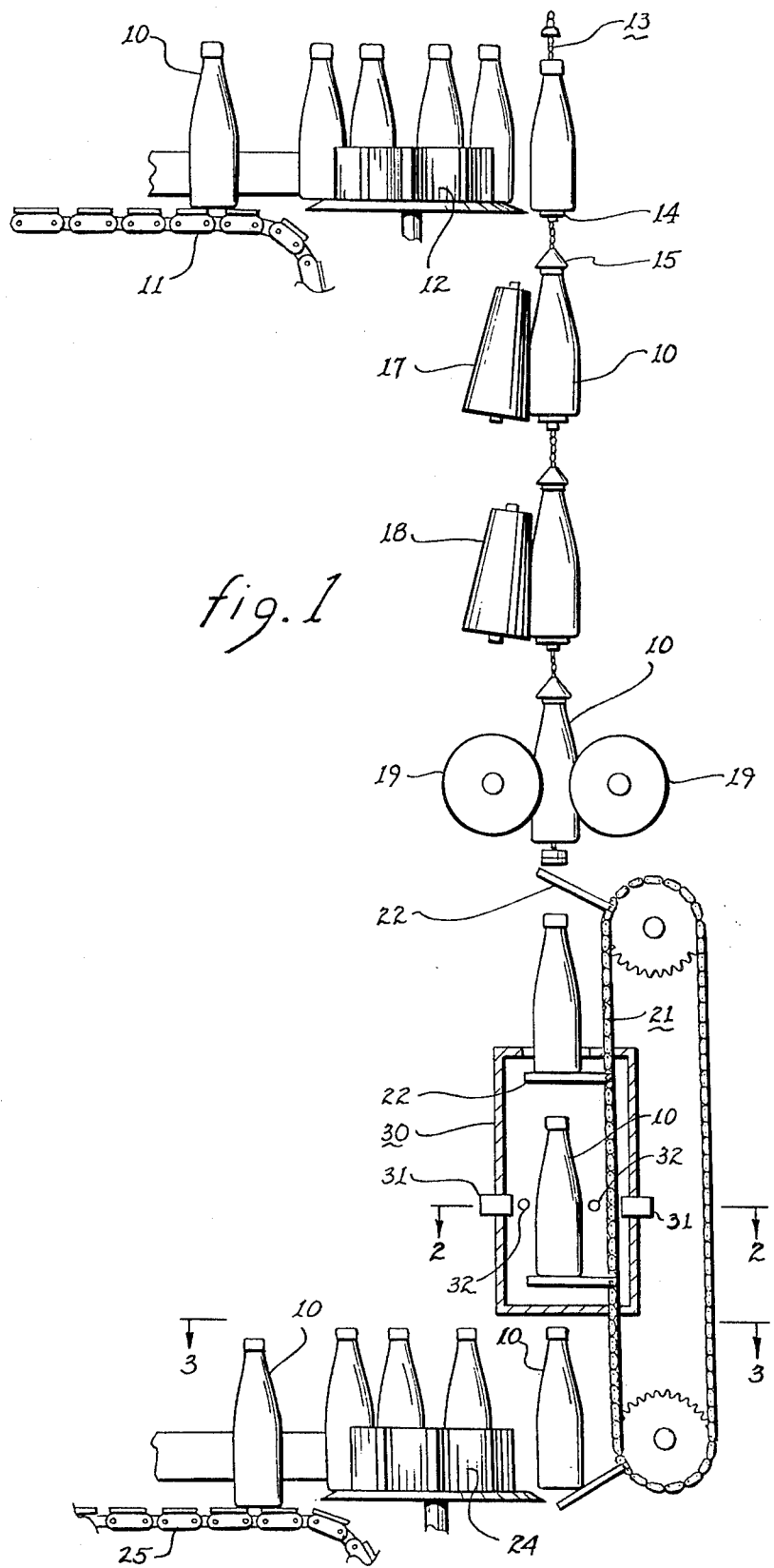
FIG. 1 is an elevational view of a portion of a conveyer line for bottled goods embodying our invention.

A portion of a conveyer driven bottling system embodying our invention is shown in FIG. 1. A train of bottles 10 filled with liquid, a beverage for example, enters the conveyer arrangement at the upper left of FIG. 1 on incoming conveyer 11. The bottles are rotated through an inlet star wheel 12 in a conventional manner and individually positioned on a vertical conveyer 13. Conveyer 13 includes a rotatable base 14 for supporting the bottles and a rotatable cap 15 for securing the bottle on the conveyer. As conveyer 13 moves bottles 10 from the top toward the bottom of FIG. 1, the bottles are brought into contact with a rotating low speed cone 17, which may be truncated as shown. Cone 17 serially contacts bottles 10 to produce rotary motion of the bottles. As conveyer 13 continues the translational motion of the bottles, each bottle is brought into contact with rotating high speed cone 18, which cone may also be truncated as shown.

The rotational motion imparted to bottles 10 by cones 17 and 18 is sufficient to bring each bottle to a rotating speed of approximately two thousand rpm. This high speed rotation has several beneficial effects. First, mixing of the contents of the bottle is ensured. For example, if a carbonated beverage were being bottled and inspected, it would be important to ensure that the syrup has been completely mixed with the carbonated water to prevent any false inspection indications caused by the non-uniformity of the contents of the bottle. Second, bottles have a tendency to pick up moisture on their surface during the bottling process. For example, as the bottles leave the soaker and undergo the rinsing process, rinsing liquid may adhere to the outside of the bottle. Additionally, bottles coming from the soaker may be relatively warm. This, mixed with the lower temperature in the bottling room and the presence of abnormal moisture in the bottling room, may cause condensation on the outside of the bottle. It is also possible for a quantity of liquid to leak onto the outside of the bottle from the filling apparatus. This is a particular possibility where carbonated beverages are being filled since occasionally the contents will foam over the bottle and adhere to the outside. The high speed rotation of the bottle will tend to strip off any adhering rinsing liquid, overflowed contents or moisture from the outside of bottle 10.

The continuing translation of a bottle 10 along conveyer 13 brings the surface of the rotating bottle into contact with brake wheels 19. The brake wheels will abruptly halt the rotation of the bottle without affecting its translational movement imparted by conveyer 13. Although the rotation of bottle 10 has been brought to a halt, the contents of the bottle will continue to rotate due to its inertia as the bottle basses through the inspection operation. The importance of this phenomenon will become apparent from the following discussion.

As each bottle 10 leaves brake wheels 19, it is transferred from conveyer 13 to a chain drive conveyer 21. Each bottle is positioned on a baffle plate 22 forming a part of conveyer 21. Conveyer 21 continues the translational movement of each bottle, and brings the bottle through the inspection apparatus 30. Inspection apparatus 30 includes a pair of light sources 31 and two pairs of photo detectors 32, 32' (see FIG. 2). The operation of the inspection apparatus will be discussed later in detail. As bottle 10 leaves the inspection apparatus, it is transferred from conveyer 21 to an outlet star wheel 24 in a conventional manner.

The bottles are rotated around outlet star wheel 24 in a manner well known in the bottling industry. The bottles are then transferred to an outgoing conveyer 25 for delivery to an accept/reject station (see FIG. 3). Those bottles which were found acceptable by inspection apparatus 30 will continue to a packaging section of the conveyer system for ultimate delivery to the consumer. Those bottles which were determined by inspection apparatus 30 to be rejected will be shunted off from the main conveyer system to a salvage operation.

Figure 2:
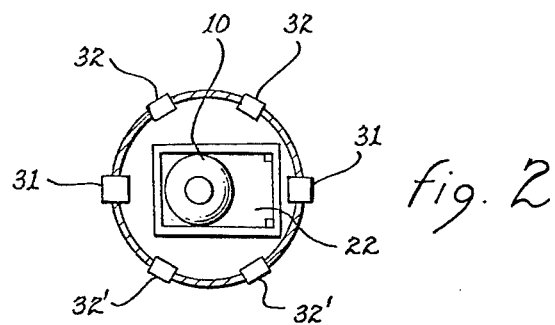
FIG. 2 is a cross-sectional view taken along lines 2—2, as shown in FIG. 1.

The inspection apparatus 30 can be readily understood from the cross-sectional view shown in FIG. 2. As illustrated, a pair of light sources 31 are arranged directly opposite one another with bottle 10 in the center. Four photo detectors 32, 32' are arranged in pairs. Each pair of photo detectors 32, 32' are positioned at equal angles from the two light sources 31, the significance of which will be explained.

It may be beneficial at this point to review the phenomenon known as the "Tyndall Effect", first observed by Faraday in 1857. He observed that when polarized light from a high intensity source was beamed through a solution and viewed at an angle to the light source, the light appeared invisible to the observer. However, when a similar light beam was beamed through a colloidal suspension, the particles of the colloid could be observed from the viewing angle. The importance of this phenomenon for the visual inspection of bottled goods resides in the fact that the contents of a bottle are normally a solution. For example, a beverage is a solution of syrup in carbonated water. However, foreign matter in the bottle, such as sand, cork particles, or glass fragments, would appear as a colloidal suspension.

The significance of the rotation and abrupt braking of bottle 10 can now be more fully appreciated. Since the contents of bottle 10 are not brought to rest immediately when the bottle is braked, the contents continue to rotate at substantial speed and any foreign matter contained within the bottle would rotate with the contents and appear as a colloidal suspension. As a result, detectors placed at the positions shown in FIG. 2, relative to light sources 21, would detect light reflected from the colloidal suspension of any foreign matter contained within bottle 10 while no such reflected light would be observed if the bottle contains a solution of its proper contents. The output of the optical detectors 32 are connected to electronic circuitry for processing as will be discussed later in conjunction with FIG. 4.

Figure 3:
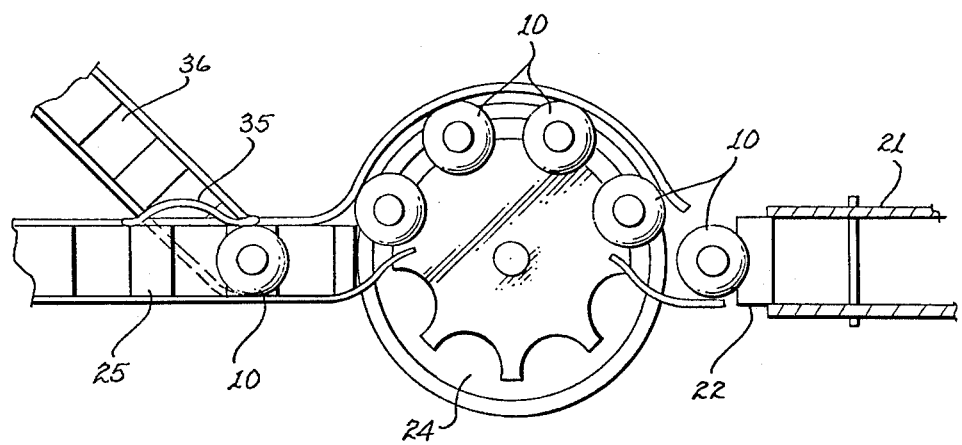
FIG. 3 is a cross-sectional view taken along lines 3—3, as shown in FIG. 1.

As the bottles leave inspection apparatus 30, they are transferred to the apparatus shown in FIG. 3. As bottle 10 leaves conveyer 21, it moves from baffle 22 into a position on outlet star wheel 24. As star wheel 24 rotates counterclockwise, bottle 10 is transferred to an outgoing conveyer 25. If the bottle has been determined to be acceptable, it will continue on conveyer 25 to be delivered to a packaging and delivery point of the bottling system. However, if bottle 10 has been found to be unacceptable, a rejection arm 35 will move to the position shown by the dotted lines, causing bottle 10 to be transferred to the reject conveyer 36 for transportation to a salvage area.

Figure 4:
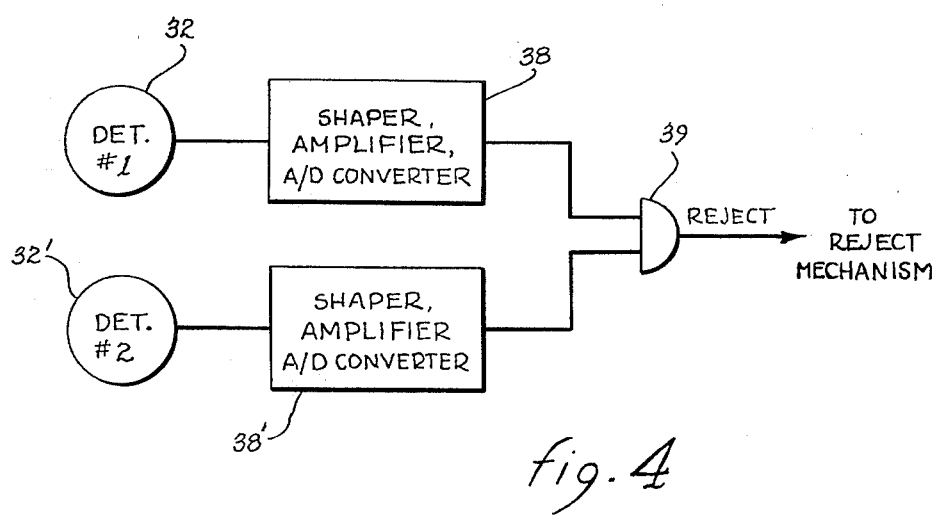
FIG. 4 is a schematic representation of circuitry for converting the detection signals into useful information.

The electronic circuitry associated with inspection apparatus 30 and the reject mechanism is shown in schematic representation in FIG. 4. The detector No. 1 and detector No. 2 shown in FIG. 4 are paired detectors 32, 32', shown in FIG. 2. This pair of detectors are located at equal angles relative to the two incoming light sources. As a result, they will pick up light reflected at the same angle from each light source. The output of paired detectors 32, 32' goes through a shaper, amplifier, and analog to digital converter 38, 38', respectively. Circuits 38, 38' will not be described in detail but include circuitry which is well known. The outputs of the two circuits 38, 38' connect to the dual inputs of an AND gate 39. If each detector produces a condition indicative of the presence of foreign matter within the contents of bottle 10, a coincident signal will appear on both inputs to AND gate 39. This will produce an output from AND gate 39 representative of a reject indication. The reject mechanism will initiate operation of rejection arm 35, shown in FIG. 3, to remove the rejected bottle, as discussed above.

A variety of conditions must be distinguished by inspection apparatus 30 to determine the acceptability of the contents of an inspected bottle. The two light sources emit energy which is sensed by the pairs of detectors. However, this energy sensed by the pairs of detectors is of a value or level below a predetermined threshold and constitutes a noise level within the circuitry attendant the detectors. Occasionally, a false signal is received by either detector of a pair but rarely by both of a pair of detectors. These false signals are screened out by the coincident signal circuitry. Where large foreign bodies, such as a cigar butt or mouse, are contained within a bottle being inspected, all the light from the inspecting beam may be screened so that paired detectors 32, 32' will receive no energy (noise). In the event no energy (noise) is received by a pair of detectors, the lack of the expected noise level within the circuitry is sensed by the circuitry and a signal is generated indicative of a reject condition. Also, no energy (noise) will be received if light sources 31 burn out, or power to inspection apparatus 30 is interrupted, etc. The circuitry of FIG. 4 is arranged to reject bottles when no energy (noise) is received since, regardless of the reason for the condition, the contents of the inspected bottle have not been inspected or have not been found free of foreign matter.

Inspection apparatus 30 must also distinguish between foreign matter adhering to the inside surface of a bottle or adhering to the outside surface thereof. Matter on the outside surface has no effect on the contents of the bottle and would therefore be acceptable. However, foreign matter adhering to the inside surface would be unacceptable since it would affect the contents of the bottle. Even if the foreign matter poses no threat to the purity of the contents, it might subsequently become dislodged and become a source of injury. For example, if the foreign matter were a glass chip, the contents would be hygenic; but if the chip dislodged from the inside surface of the bottle, it could be swallowed by a consumer. Fortunately, a foreign body on the inside surface of a bottle induces eddy currents in the liquid contents as they rotate past that point on the inside surface. These eddy currents in turn release bubbles in the carbonated contents. These bubbles will appear to inspection apparatus 30 as small bodies of foreign matter, which will be detected and result in rejection of the bottle. A foreign body adhering to the outside surface of the bottle will induce no such eddy currents and will be ignored by inspection apparatus 30.

To produce a reliable result, inspection apparatus 30 must be unaffected by spurious optical or electrical noise, which is always present in optical and electrical equipment. Because a pair of sources 31 simultaneously transmit inspection light beams, the signals produced by the paired detectors 32, 32' will be coincident when the beams are reflected by a foreign body in the contents but will appear at only one detector if they are produced by optical or electrical noise. Since AND gate 39 energizes the rejection mechanism only in response to coindicent signals, the inspection process is isolated from the effects of spurious noise.

If the contents of the inspected bottle only contain a solution, such as a foreign matter free beverage, the light from sources 31 will produce no rejection signal at detectors 32, 32' and the inspected bottle will be accepted. Should any small foreign body, including eddy current induced bubbles, be present in the contents of the inspected bottle, the foreign body will reflect light to be detected by detectors 32, 32'. As discussed, this will cause the inspected bottle to be rejected.

The prior art inspection systems have encountered problems with bottles having fluted sides or carrying advertising indicia. If the systems were made sensitive to variations in the amplitude pattern of the inspection light beam, the variations produced by the fluted sides or the advertising indicia would induce unwarranted rejections. If the systems were desensitized to avoid this, a bottle containing foreign matter producing a marginal rejection indication would be improperly accepted. The effect of background light is related to these problems because it affects the sensitivity of the inspection apparatus. The presence of background light reduces the contrast of the inspection beam with respect to ambient lighting in the prior art systems. This reduces the system's sensitivity, which reduces the reliability of the inspection process.

Although baffles 22 will be effective to screen a substantial portion of the background light of inspection apparatus 30, some background light will inevitably be present during the inspection. But, the signal detected by detectors 32, 32' and resulting from background lighting, will be essentially constant. Changes in the signal caused by surface irregularities, such as flutes or advertising indicia, will be similarly constant. Signals emanating from the liquid contents of the bottle being inspected will be variable, however, due to the rotation of the contents. Since the circuitry of circuits 38, 38' can distinguish a variable signal from a constant signal, the effects of background lighting and irregularities in the surface of the bottles are ignored. Additionally, inspection apparatus 30 discriminates from transient effects by the redundancy requirement of detectors 32 and 32'. Since transient effects would not produce coincident signals in both pairs of detectors, the redundancy of paired detectors further increases the reliability of inspection apparatus 30.

In summary, particulate foreign matter suspended within a bottle undergoing inspection will cause a reflection of the light from a light source to a pair of detectors. The coincident detection by the pair of detectors of the reflected light, will result in the generation of a reject signal by the circuitry illustrated in FIG. 4. During inspection of bottles free of foreign matter, a degree of energy will be transmitted from the light sources to the detectors, which energy is of a very low level and constitutes "noise" in the vernacular of an electronic engineer. This energy level is detected by the detectors and sensed by the attendant circuitry but as it is below a predetermined threshold, the energy will not constitute a signal of the type representative of particulate matter within the contents of a bottle under inspection. However, the presence of this level of energy constitutes a representation to the associated circuitry that the system is in operation. In the event of malfunction of a light source(s), the noise level of the associated pair of detectors will be absent. Such absence is sensed by the circuitry and an appropriate indication is generated by the circuitry. Similarly, should a foreign object be lodged within a bottle undergoing inspection, which is of a size sufficient to completely blank the transmission of energy from a light source of a pair of detectors or preclude transmission of reflected light to a pair of detectors, the noise level will be absent and such absence is sensed by the associated circuitry and an appropriate signal is generated by the circuitry. The absence of a low level energy input to the detectors and the attendant absence of a noise level within the attendant circuitry is indicative of either a malfunctioning light source or a large object within the bottle under inspection, both of which conditions constitute a basis for rejection as the bottle has either not been inspected or has been inspected and found unacceptable. Thus, the present invention provides an indication of bottles free of suspended foreign matter; bottles containing foreign matter; and equipment malfunction.

Even greater operational reliability can be obtained where the additional expense justifies it. The single ring of sources and detectors shown in the drawing may be duplicated either above and/or below the disclosed ring. This would introduce any degree of redundancy desired. The constant output of light source 31 could also be replaced by a pulsed source to produce a strobe effect. The pulsed outputs from the pair of sources could either be synchronized or intentionally made asynchronous. Further, although the disclosed sources 31 were, by implication, of similar type, they need not be so. For example, one source may emit ultraviolet light and the other might emit light in the visual or infra red range. Thus, the reliability and redundancy may be varied as required to meet the demands of individual systems. Since the translational speed of bottles on a bottling conveyer, and hence through the inspection process, is appreciable in modern bottling plants, the necessity for high reliability can be appreciated. That is, unwarranted rejections introduce unnecessary expense while unwarranted acceptances endanger the consumer and subject the bottler to unnecessary liability.

The system disclosed in representational only and should not be interpreted as any limitation on the invention claimed. For example, although the translational conveyer systems which move the bottles past the inspection point are disclosed as being vertical, it should be apparent that such a conveyer arrangement could be adapted for horizontal translation as well. Various other modifications and and alterations could be made by those skilled in the art without departing from the spirit and scope of our invention.

We claim:
1. A method for inspecting the contents of filled bottled goods and detecting the presence of foreign matter therein without affecting the translational speed of the bottled goods along a conveyer, said method comprising the steps of:
 a. translating a plurality of filled bottles along a conveyer;
 b. rotating each translating bottle and the contents thereof;
 c. stopping the rotation of each bottle abruptly enough to inspire relative rotation between the contents and the bottle while continuing the translational movement of the bottle along the conveyer;
 d. transmitting radiant energy from a stationary source through each bottle and the rotating contents thereof as the bottle continues its translational movement along the conveyer;
 e. producing a plurality of detection signals from stationary detector means in response to the radiant energy transmitted through each bottle and the contents thereof during translational movement of the bottle and its contents past the stationary detector means;
 f. generating a plurality of output signals responsive to the plurality of detection signals and indicative of the transmitted radiant energy intercepted by the bottle and the contents thereof;
 g. comparing the plurality of output signals with one another to provide a compared signal reflective of the coincidence of the detection signals; and
 h. determining the presence of foreign matter in each bottle from the compared signal.

2. The method as set forth in claim 1 including the steps of:
 a. identifying each bottle determined to have foreign matter present therein; and
 b. removing each identified bottle from the conveyer.

3. Apparatus for inspecting bottled goods to detect the presence of foreign matter therein while the bottled goods move along a conveyer, said apparatus comprising in combination:
 a. a conveyer for movably translating a plurality of filled bottles;
 b. means for selectively rotating each bottle and the contents thereof as the bottle is translated by said conveyer;
 c. means for stopping the rotation of each bottle abruptly enough to inspire relative rotation between the contents and the bottle while continuing the translational movement of the bottle along said conveyer;

d. stationary scanning means for transmitting radiant energy through each bottle and the rotating contents thereof as the bottle continues its translation along said conveyor past said scanning means;
e. stationary detector means for producing a plurality of detection signals in response to the radiant energy transmitted through each bottle and the contents thereof during passage of the bottle and the contents thereof past said detector means;
f. means for generating a plurality of output signals responsive to the plurality of detection signals and indicative of the transmitted radiant energy intercepted by the bottle and the contents thereof;
g. means for comparing the plurality of output signals to one another to provide a compared signal reflective of the coincidence of the detection signals; and
h. means responsive to said compared signal for determining the presence of foreign matter in each bottle.

4. The apparatus as set forth in claim 3 further including:
a. means for identifying each bottle determined to have foreign matter therein; and
b. means for removing each identified bottle from said conveyer.

5. The apparatus as set forth in claim 4 wherein said scanning means is located in proximity to said conveyer and is fixedly positioned so that each bottle translates past said scanning means as the radiant energy is transmitted therethrough.

6. The apparatus as set forth in claim 5 wherein said detector means is fixed in position relative to said scanning means.

7. The apparatus as set forth in claim 6 wherein said detector means includes a plurality of photovoltaic cells.

8. The apparatus as set forth in claim 7 wherein said scanning means includes beam means for generating a plurality of radiant energy beams.

9. The apparatus as set forth in claim 8 wherein said beam means includes a plurality of visual light sources.

10. The apparatus as set forth in claim 9 wherein said plurality of visual light sources and said plurality of photovoltaic cells are located around the periphery of a circle and are positioned facing the center thereof.

11. The apparatus as set forth in claim 10 wherein said plurality of visual light sources include a pair of diametrically opposed visual light sources.

12. The apparatus as set forth in claim 11 wherein said plurality of photovoltaic cells includes a plurality of redundant photovoltaic cells responsive to each of said pair of visual light sources.

13. The apparatus as set forth in claim 12 wherein said plurality of redundant photovoltaic cells includes a pair of photovoltaic cells located in each semicircle intermediate said pair of visual light sources.

* * * * *